United States Patent [19]

Geluk

[11] Patent Number: 4,856,040

[45] Date of Patent: Aug. 8, 1989

[54] APPARATUS AND METHOD FOR SLIT RADIOGRAPHY WITH DIFFERENT X-RAY ENERGIES

[75] Inventor: Ronald J. Geluk, Nootdorp, Netherlands

[73] Assignee: B.V. Optische Industrie "De Oude Delft", Delft, Netherlands

[21] Appl. No.: 212,530

[22] Filed: Jun. 28, 1988

Related U.S. Application Data

[63] Continuation of Ser. No. 875,409, Jun. 17, 1986, abandoned.

[30] Foreign Application Priority Data

Jun. 21, 1985 [NL] Netherlands ............... 8501795

[51] Int. Cl.⁴ ............................... G21K 5/10
[52] U.S. Cl. ........................ 378/146; 378/145
[58] Field of Search ........................... 378/146

[56] References Cited

U.S. PATENT DOCUMENTS

4,677,652  1/1987  Duinker ........................ 378/146
4,731,807  3/1988  Plessis ......................... 378/146

Primary Examiner—Craig E. Church
Attorney, Agent, or Firm—Louis E. Marn

[57] ABSTRACT

An apparatus and method for slit radiography, in which a body to be irradiated is scanned at least twice by means of a planar, fan X-ray beam emitted from an X-ray source (1) via a slit diaphragm (2), the hardness of which beam increases with each next scanning motion, in which an X-ray detector (6) mounted behind the body collects the radiation passed, sections of detection means (10), which sections are juxtaposed in the longitudinal direction of the X-ray detector, produce electrical signals depending upon the radiation collected by the respective X-ray detector sections, which signals are sampled during each scanning motion and are stored in a memory, and the diaphragm (2) includes controllable elements juxtaposed in the longitudinal direction of the slit in a plurality corresponding to that of the sections of the detection means, which controllable elements are each operative to locally block the slit diaphragm during a next scanning motion if a stored signal produced by the corresponding section of the detection means during a preceding scanning motion exceeds a predetermined value.

16 Claims, 2 Drawing Sheets

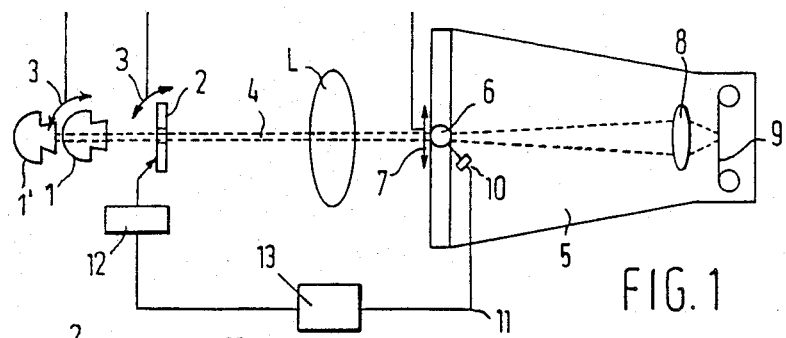
FIG. 1
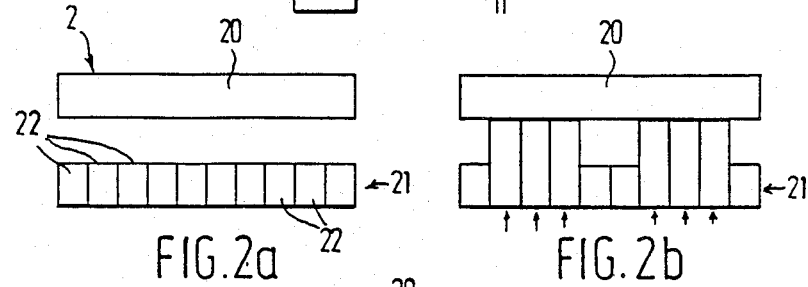
FIG. 2a
FIG. 2b
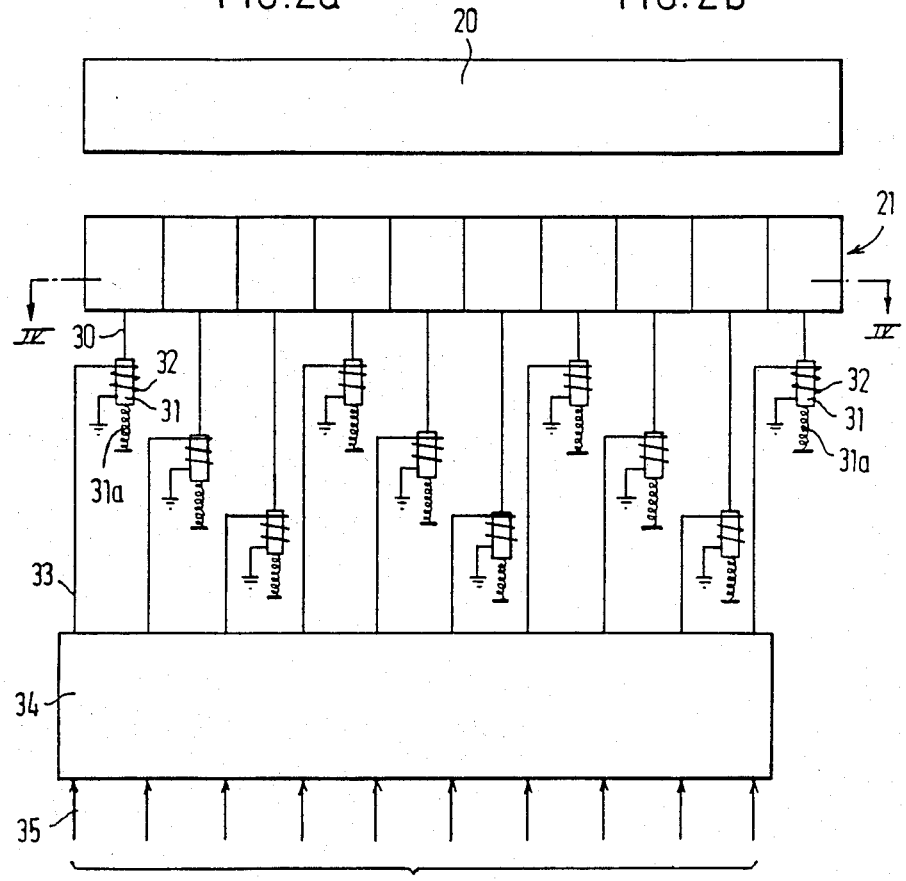
FIG. 3

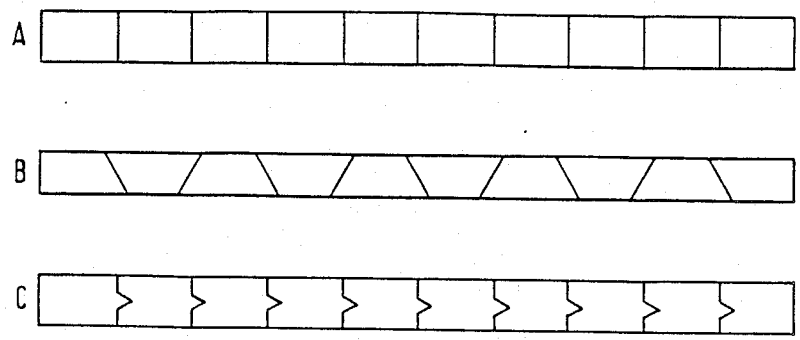
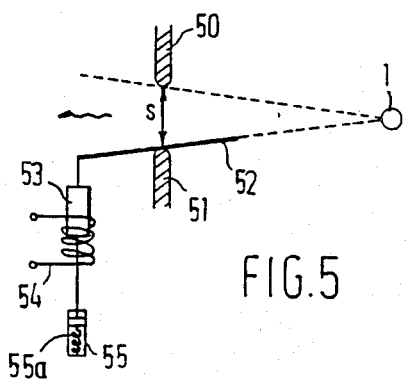
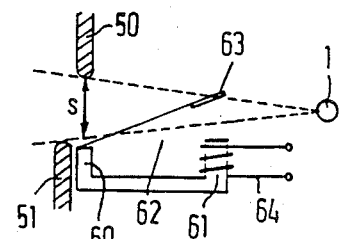
FIG.4
FIG.5
FIG.6
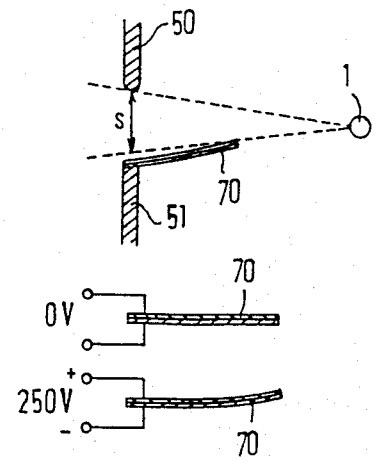
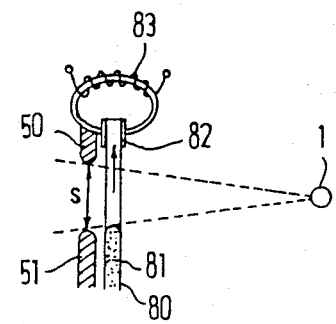
FIG.7
FIG.8

APPARATUS AND METHOD FOR SLIT RADIOGRAPHY WITH DIFFERENT X-RAY ENERGIES

This is a continuation, of application Ser. No. 875,409, filed June 17, 1986 now abandoned.

The invention relates to an apparatus for slit radiography comprising at least one X-ray source, an X-ray detector disposed behind a body being irradiated to collect the radiation having passed through the body, and a slit diaphragm disposed between the X-ray source and the body being irradiated to form a planar, fan X-ray beam, in which for obtaining a complete X-ray shadow image of the desired part of the body the fan beam performs at least one scanning motion, and detection means are provided to coact with the X-ray detector, which detection means comprise a plurality of sections arranged in juxtaposition in the longitudinal direction of the striplike portion of the X-ray detector irradiated via the slit diaphragm, each section being adapted to produce an electrical signal depending upon the radiation instantaneously incident on the associated section of the X-ray detector, the slit diaphragm comprising a plurality of sections arranged in juxtaposition in the longitudinal direction of the slit, which plurality corresponds to that of the sections of the detection means, each of which section coacts with at least one controllable element, means being provided to control these elements.

Such an apparatus is disclosed in applicants' copending U.S. patent application Ser. No. 713,198, now U.S. Pat. No. 4,715,056.

The known apparatus comprises an elongate X-ray detector mount to have its entrance surface collect at all times the radiation having passed through the slit diaphragm and the body being irradiated. The assembly of detector, X-ray source and diaphragm is so moved relative to the body that the desired part thereof is scanned. The detector converts the X-rays collected into an intensified light beam used for exposing a photographic film. During the scanning motion the detection means measure the amount of light incident on each associated section of the X-ray detector, while the corresponding controllable elements in the slit diaphragm are so controlled in dependence upon this amount of incident light that they section-wise block the slit to a greater or lesser extent. This permits an instantaneous, section-wise control of the intensity of the radiation having passed through the body being irradiated, so that the recorded X-ray image will not include regions that fail to show detail on account of too large amounts of such radiation resulting in, for example, the film on which the image is recorded having too high a density in those regions.

It is known in radiography to preferably select the hardness of the X-rays in dependence upon the type and the amount of tissue to be irradiated. The hardness of X-rays is determined by the high voltage applied to the X-ray source and is usually expressed in kV, the higher the kV value the harder the X-rays.

Problems arise if a single radiograph is to show parts of the body that would preferably need irradiation with X-rays of different hardnesses. Such problems occur, for example, in thorax radiography, in which the lungs are preferably to be radiographed with low hardness X-rays so as to permit small differences in density in the lung tissue to be displayed with sufficient contrast. The high voltage to be applied to the X-ray source for such purposes will be, for example, 60 kV. However, other tissue to be displayed in thorax radiography, such as the heart and the spinal column, is preferably to be irradiated with X-rays of higher hardness, the voltage applied to the X-ray source, being, for example, 100–140 kV. Should, in thorax radiography, a body be successively irradiated with X-rays of different hardnesses, the final radiograph would only show detail in the regions irradiated with high hardness X-rays, while the other regions, such as the lungs, would not show any detail and be displayed completely black as too much radiation is passed by these regions.

It is an object of the invention to provide an apparatus that permits the making of a radiograph by means of X-rays of different hardnesses without certain portions of the radiograph becoming so dark that no details can be made out.

To this end, the invention provides an apparatus of the above type in which the X-ray source is arranged for performing at least two scanning motions and the X-rays emitted during the subsequent scanning motions each time have a higher hardness, in which the electrical signals of the sections of the detection means are sampled during each scanning motion, the sampled signal values are stored in a memory and during each next scanning motion the corresponding signals of the preceding scanning motion are retrieved from the memory to be applied to the control means, which control means energize those controllable elements that each time correspond to the section of the detection means that produced an electrical signal exceeding a predetermined value at a corresponding instant during the preceding scanning motion, the energizing signal being adapted to cause the controllable elements to block section-wise the associated sections of the slit diaphragm.

In accordance with the invention, during two or more subsequent scanning motions the body under examination is irradiated with X-rays of each time higher hardness, in which those regions of the shadow image that, according to the output signal of the detection means, already received a sufficient amount of radiation during a stage in the preceding scanning motion for providing an image of sufficient contrast, do not receive any further radiation during the corresponding stage in the next scanning motion as the associated sections of the slit diaphragm are blocked. In this manner it is possible to combine two or more images of a body made with X-rays of different hardnesses into a single radiograph showing each tissue with optimum contrast.

It is observed that applicants' older Dutch patent application No. 84,01946 already discloses a system for forming a shadow image of a body by irradiating this body with X-rays of different hardnesses. However, in this system a separate electronic image is formed at each level of hardness, which images are subsequently combined into a single image, for example by means of a computer. In accordance with the present invention, this single image is obtained without any additional processing.

The invention also relates to a method for slit radiography, in which X-rays are emitted from at least one X-ray source and are formed into a planar, fan X-ray beam by a slit diaphragm disposed between the X-ray source and the body being irradiated, an X-ray detector disposed behind the body being irradiated collects the radiation having passed through the body, and for obtaining a complete X-ray shadow image the desired part of the body is scanned at least once, in which sections of detection means coacting with the X-ray detector, which sections are arranged in juxtaposition in the longitudinal direction of the strip-like portion of the X-ray detector irradiated via the slit diaphragm, produce electrical signals depending upon the radiation instantaneously incident on the associated section of the X-ray detector, the slit diaphragm comprising a plurality of controllable elements arranged in juxtaposition in the longitudinal direction of the slit, which plurality corresponds to that of the sections of the detection means; in which the X-ray source performs at least two scanning motions and during the subsequent scanning motions X-rays of each time higher hardness are emitted, the electrical signals of the sections of the detection means being sampled during each scanning motion, the sample signal values being stored in a memory and during each next scanning motion the corresponding signals of the preceding scanning motion being retrieved from the memory to energize those controllable elements that each time correspond to the section of the detection means that produced an electrical signal exceeding a predetermined value at a corresponding instant during the preceding scanning motion, the controllable elements section-wise blocking the slit diaphragm.

As in the apparatus according to the invention a relatively long period of time up to about one second, can pass between successive scanning motions, movements of the body being irradiated during that period of time might cause problems. However, as each part of the body being irradiated is recorded only once, the chances of unsharpness due to such movements are very small. Double exposure can occur only at the contours of two recording regions, but this does not result in unsharpness of the image. For example, in thorax radiography the contour of the heart may be visible at two different positions in the radiograph but this will not interfere with the examination of the radiograph and may even be useful in certain diagnoses.

The invention will be described in greater detail hereinafter with reference to the accompanying drawings, in which:

FIG. 1 schematically shows in sideview an example of an apparatus for slit radiography in accordance with the invention;

FIGS. 2a and 2b schematically show examples of a slit diaphragm for use in the apparatus of FIG. 1;

FIG. 3 shows the manner in which the slit diaphragm of FIGS. 2a and 2b can be partly blocked;

FIG. 4 shows a number of embodiments of a slit diaphragm according to FIG. 3 in cross-sectional view through the line IV—IV;

FIG. 5 shows a slit diaphragm and the manner in which the effective slit width can be locally controlled; and FIGS. 6, 7 and 8 show variants of FIG. 5.

Figure 10:
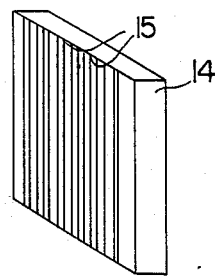
FIGS. 9, 10 and 11 show variants of the X-ray detector of the embodiment of FIG. 1.

FIG. 1 schematically shows in sideview an example of an apparatus for slit radiography comprising at least one X-ray source 1 adapted to perform, together with a slit diaphragm 2, a pivotal motion as indicated by arrows 3. Slit diaphragm 2 causes a planar, fan X-ray beam 4, which performs a scanning motion in response to the pivotal motion 3 performed by X-ray source and slit diaphragm. X-ray source 1 can be arranged for generating X-rays of different, for example two, radiation energies, but self-evidently there can alternatively be provided a number, for example two, of X-rays sources and each generating X-rays of a different radiation energy and each adapted to perform a pivotal motion 3 for successively producing via diaphragm 2 fan X-ray beams of different energies during subsequent scanning motions.

It is observed that a scanning motion of the X-ray beam can alternatively be achieved if the X-ray source is stationary and the slit diaphragm performs a translatory motion normal to the longitudinal direction of the slit, supplemented by a pivotal motion if desired, or if the diaphragm is stationary and the X-ray source performs a translatory motion supplemented by a pivotal motion is desired.

A housing 5 is disposed opposite to the slit diaphragm at sufficient distance therefrom to allow a body L to be positioned therebetween, which housing 5 includes an X-ray detector 6 having an entrance surface of sufficient size to collect the radiation having passed through the body being irradiated at all times during the pivotal motion of the X-ray source and the slit diaphragm.

In the example shown, an elongate tubular detector of the proximity focus type is used, which converts the X-rays collected into a light image while performing a vertical motion as shown by arrow 7 in synchronism with the pivotal motion of the X-ray source.

The successive strip-like light images provided by the detector are projected via a schematically shown lens system 8 onto a film 9 for forming a complete image from the successively projected strip-like images.

A light detection device 10 is mounted in the vicinity of X-ray detector 6, which device 10, seen in a direction normal to the plane of the drawing, includes a plurality of sections arranged in juxtaposition, which sections each measure the amount of light generated by a corresponding, opposite portion of the exit surface of the X-ray detector. To this end, in the example shown, the light detection device moves with the X-ray detector. The amounts of light measured by the sections of the light detection device during the scanning motion are converted in known per se manner into electrical signals, which signals are periodically sampled and applied through a line 11 to a schematically shown memory 13 in which the output signal of each section for each sampling is stored at a separate memory location. During the next scanning motion the signals stored in memory 13 are applied to control means 12. The control means are arranged for locally blocking the slit diaphragm. To this end, the slit diaphragm is composed of a plurality of sections corresponding to the plurality of sections of the light detection device. In each of the diaphragm sections and diaphragm slit can be blocked in one of the manners to be described later on.

In illustration of the principle underlying the present invention, the thorax radiography example used above is now described in greater detail. First the film is exposed to the image produced by the soft X-radiation for optimally displaying the lungs. During this first scanning motion the slit diaphragm is fully open.

Simultaneously, at the exit surface of detector 6 detection device 10 registers at which positions the light level is high enough for causing sufficient film density. These positions are stored in digital memory 13 for each sampling during the first scanning motion.

The result is an electronic image of the portions recorded by means of soft radiation on the film with sufficient contrast. This image may consist of, for example, 20×30 pixels if the detection means are sampled 30 times in vertical direction and the detection means consist of 20 sections. Subsequently a second image can be formed on the same film, now with X-radiation of higher hardness, by means of which the heart and the spinal column can be displayed with sufficient contrast. To avoid double exposure in the area of the lungs, during this second scanning motion the controllable elements in the slit diaphragm are so controlled by control means 12, which to that end receive from memory 13 the electrical signals produced by the detection device at a corresponding instant during the preceding scanning motion, that the area of the lungs is fully shielded from X-rays. Consequently, this shielding takes place on the basis of the information provided by the image that was electronically recorded during the first scanning motion.

The result is a single picture showing the lungs as well as the denser body parts with optimum contrast. Self-evidently, in this manner the film density it likewise kept within satisfactory limits. Furthermore, self-evidently the light detection device is so disposed that it does not obstruct the radiation between X-ray detector 6 and lens system 8.

FIG. 2a schematically shows an example of a slit diaphragm for an apparatus according to the invention. The diaphragm includes an upper member 20, which may be of lead, and a lower member 21 having sections 22 adapted for movement relative to each other into the direction of the upper member. Sections 22 may likewise be of lead.

FIG. 2b shows a possible position of movable sections 22 after radiographing with a first, low X-ray energy. The sections indicated by arrows have moved into the direction of the upper member of the diaphragm so as to locally block the slit.

In the example shown, ten movable sections are used which correspond to ten light detection sections.

In thorax radiography satisfactory results can be achieved by means of such a number of sections. Self-evidently if desired a different number of sections may be employed.

FIG. 3 schematically shows the manner in which the slit diaphragm sections shown in FIG. 2 can be controlled. The sections of diaphragm member 21 are each connected through a member 30 attached thereto, for example a rod, to a, for example, soft iron coil core 31 adapted for movement within a coil 32 and kept in its rest position by reset means, such as spring means 31a or a magnet.

Each coil is energized through an output 33 of a control device 34. The control signal presented at each output 33 depends on an input signal applied to a corresponding input 35 of the control device, which input signal is supplied from the associated memory location of memory 13. The intensitiy of the current traversing a coil determines the position of the associated soft iron core and hence whether the diaphragm section coupled thereto is open or closed.

It is observed that in the example shown only one of the members of the slit diaphragm includes movable sections. Self-evidently it is possible to provide both slit diaphragm members with movable sections.

It is further observed that the movable sections of a diaphragm member are mounted jointly in a support member. The structure of such a support member is obvious to the worker in the art and will therefore not be discussed.

The movable sections of the one slit diaphragm member as shown in FIGS. 2a, 2b and 3 may be of rectangular section, as shown in FIG. 4A, which is a cross-sectional view through line IV—IV in FIG. 3. In this embodiment, leakage of X-rays through interspaces or transitions between the sections could lead to stripes in the final radiograph. To reduce the chances thereof, the slit diaphragm sections may each be of trapezoidal section as shown in FIG. 4B, which is a cross-sectional view corresponding to that of FIG. 4A. Other variants are possible, such as the one shown in FIG. 4C, in which the sections interlock through tongues and grooves.

FIG. 5 schematically shows in sideview a further embodiment of a slit diaphragm suited for use in an apparatus according to the invention. This embodiment employs two fixed diaphragm members 50 and 51 defining a fixed slit S. For guidance, X-ray source 1 is schematically shown in FIG. 5.

A plurality of juxtaposed, elongate blocking elements is disposed in slit S, one of which is shown in FIG. 5 at 52. Blocking element 52 extends through slit S and is mounted for pivotal movement relative to one of the fixed diaphragm members, in this example lower member 51, or relative to a suitably mounted support. Element 52 has its one end coupled to a movable soft iron core 53 of a coil 54 in the manner described above with reference to the sections shown in FIG. 3. The soft iron core is further connected to a damping member 55 operative to prevent core 53 from overshooting upon energization of the coil. Furthermore, a reset spring is provided, which in this example is a compression spring 55a mounted within the damping member.

Blocking element 52 has its opposite end facing, in this example, the X-ray source and can intercept the X-ray beam from source 1 to slit S under the control of coil 54.

The blocking elements may be of lead but also of any other suitable material that attenuates X-rays, such as soft iron, bronze, gold and the like.

FIG. 6 shows a variant of FIG. 5. In the embodiment of FIG. 6 the fixed members of the slit diaphragm are again denoted by 50 and 51. A U-shaped soft iron yoke is mounted between X-ray source 1 and the slit diaphragm, which yoke has its one leg 60 located adjacent the slit diaphragm and its other leg 61 spaced a distance therefrom. A resilient tongue 62 is attached to the top of leg 60, which tongue extends obliquely upwards and has its free end provided with a plate of magnetic material, for example magnet steel, which plate is situated above leg 61. A coil 64 is wound about leg 61 and is energizable by a control device comparable to control device 34 of FIG. 3. Depending upon the control of coil 64, plate 63 is attracted to a greater or lesser extent by leg 61 to intercept to a lesser or greater extent the X-rays from source 1 to slit S.

It is observed that for controlling the blocking of slit S over its entire length, a plurality of such yokes with resilient tongues as described is mounted in juxtaposition.

It is further observed that, in principle, the yoke may be so mounted that the leg carrying coil 64 is located adjacent the diaphragm, the resilient tongue being attached to the leg remote from the diaphragm.

Furthermore, in both cases the yoke may be located on the other side of the diaphragm, i.e., the side remote from the X-ray source.

Yet another possibility of moving the blocking elements in accordance with FIGS. 2–4 from a position in which the slit is blocked to a position in which this slit is open and vice versa, is to connect each one of the elements through, for example, a rod via a suitable eccentric to a miniature motor operative to move the elements via the rod.

FIG. 7 shows another variant of FIG. 5. A plurality of rod-shaped piëzoelectric elements, one of which is shown in FIG. 7 at 70, is mounted in juxtaposition on at least one of the fixed members of the slit diaphragm or on a suitable support. Such an element is straight in the rest position but arches in response to the application of a voltage across its opposing sides. This is shown in FIG. 7. This known effect can be used for controllably blocking the slit diaphragm.

Such elements are available under the name of Bimorph Flexure Element.

As such elements usually contain lead, they can be readily used for the object contemplated. However, should the attenuating effect prove insufficient, the piëzoelectric elements may be coated with an X-ray absorbing material.

FIG. 8 shows yet another variant, in which use is made of a magnetic liquid for blocking the slit diaphragm.

A plurality of flat, hollow tubes 80 of plastics or glass containing a known per se magnetic liquid 81 is mounted in juxtaposition between X-ray source 1 and the slit diaphragm. Pole pieces 82 are provided at the top of each tube, which pole pieces are interconnected by a coil core about which a coil 83 is wound. Upon coil energization, the magnetic liquid is attracted by the pole pieces to move in front of slit S, thereby locally intercepting the X-rays from X-ray source 1.

It is observed that the above describes only a few examples of methods for locally blocking the slit-shaped opening of a slit diaphragm. Other methods will be readily obvious to the worker in the art after reading the foregoing.

The example of an apparatus for slit radiography shown in FIG. 1 employs an elongate proximity focus tube as an X-ray detector. Such a tube comprises an elongate cathode provided in known manner with a material operative to convert X-radiation into light quanta, and with a material responsive to light quanta for releasing electrons. These electrons are drawn by an electric field towards an anode mounted parallel to the cathode and likewise of strip-like configuration, which anode is responsive to the electrons incident thereon for forming a light image.

The light detection device may consist of a series of photosensitive elements placed within the housing of the X-ray detector, or, alternatively, exterior of this housing. In the latter case, the light detection device may consist of a series of lenses each viewing a section of the anode and each followed by a photomultiplier tube.

Figure 9:
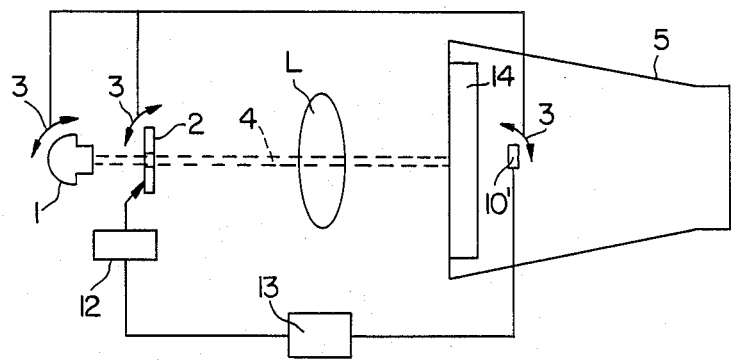
Figure 11:
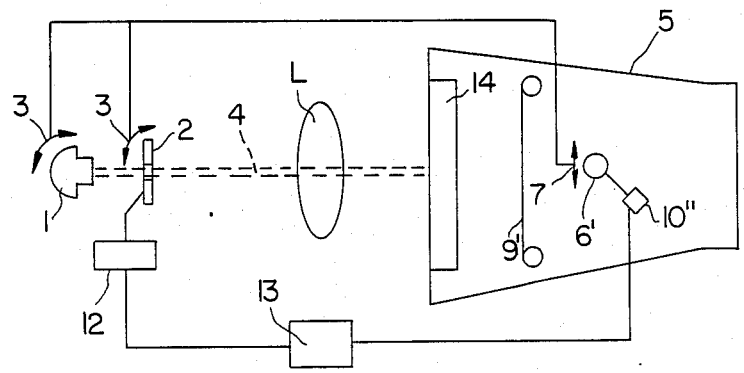

As shown in the FIGS. 9, 10 and 11, the invention is also applicable to an apparatus for slit radiography that does not include a detector that moves with the pivotal motion of the X-ray source and the slit diaphragm but includes instead a large X-ray screen 14 exposed by the X-ray source when the latter performs its scanning motion. In the FIGS. 9 and 11, like reference numerals are used for like parts of the apparatus of FIG. 1. In the embodiment according to FIG. 9, the light detection device 10′ performs a scanning motion corresponding to that of the X-ray source at the back of the X-ray screen. Alternatively in the embodiment of FIG. 10 which in a perspective view shows only the X-ray screen 14 placed in the housing 5, the light detection device is composed of, vertically arranged strip-like photoconductors 15 that absorb little X-radiation and are disposed at the front of the X-ray screen, where, in fact, light is produced as well. When an X-ray screen according to FIG. 10 is used, the photoconductors 15 are connected to the detection device 10.

In the embodiment of FIG. 11 film cassette 9′ in a light-tight fashion is placed directly behind the X-ray screen, and mounted behind the film cassette, an X-ray detector 6′ performing a scanning motion and provided with a light detection device 10″ as described above is used. Alternative a second large X-ray screen converting the X-radiation passed by the film cassette into light and followed by a light detection device performing a scanning motion, may be used. In that case, however, there is the drawback of the film cassette affecting the X-ray spectrum but the advantage of the local blocking of the slit-shaped opening of the slit diaphragm is maintained.

The invention is further applicable to systems in which the scanning motion is a result of a rotation instead of a linear movement normal to the longitudinal direction of the slit.

All such modifications are deemed to fall within the scope of the present invention.

What I claim is:

1. An improved process for X-ray imaging a body using slit radiography, which comprises:

passing a planar X-ray beam of a first intensity through said body;

detecting X-ray radiation passing through said body in a plurality of sections along a longitudinal direction of said planar X-ray beam;

converting said detected X-ray radiation into electrical signals representative of intensity thereof;

storing said electrical signals;

generating a planar X-beam of a second intensity harder than said X-ray beam of said first intensity; and attenuating said X-ray beam of said second intensity in each of said sections prior to passage through said body in response to said stored electrical signals should a respective electric signal exceeds a predetermined value at a corresponding instant during passage of said X-ray beam of said first intensity through said body.

2. An apparatus for slit radiography, which comprises:

an X-ray source;

an X-ray detector means for collecting radiation passing through a body to be radiographed;

a slit diaphragm means positioned between said X-ray source and said body for forming a substantially planar X-ray beam;

a plurality of attenuating elements positioned along said slit diaphragm means forming a plurality of attenuating section;

means for successively scanning said body with planar X-ray beams of increasing hardness;

memory means connected to said X-ray detector means for storing an electric signal responsive to radiation collected on said X-ray detector means respresentative of intensity of said thus collected radiation corresponding to respective attenuating sections during a first scanning of said body by said planar X-ray beam; and means responsive to said memory means for controlling each of said attenuating elements during a subsequent scanning of said body by said planar X-ray beam of increased hardness if a respective electric signal exceeds a predetermined value at a corresponding instant during a first scanning of said body.

3. The apparatus according to claim 2 wherein said X-ray detector means is a stationary X-ray screen and comprises juxtaposed strips of a photoconductive material adsorbing little X-radiation, said strips being disposed on a side of said X-ray screen facing said body being irradiated extending normal to scanning direction.

4. The apparatus according to claim 2 and further including a plurality of X-ray sources emitting X-rays of a different hardness.

5. The apparatus according to claim 2 or 4 wherein said plurality of attenuating elements are juxtaposed and movable relative to each other in a direction normal to a longitudinal direction of said slit diaphragm, said attenuating elements being coupled to a movable core of a coil energized by a control device.

6. The apparatus according to claim 5 wherein said attenuating elements are trapezoidally-shaped.

7. The apparatus according to claim 5 wherein said attenuating elements interlock in tongue and groove relationship.

8. The apparatus according to claim 2 or 4 wherein each attenuating element extends essentially normal to a longitudinal direction of said slit diaphragm for movement into said planar X-ray beam in response to said control means.

9. The apparatus according to claim 8 wherein said attenuating elements are mounted to said slit diaphragm on a parallel support therefor for pivotal movement at a point between ends thereof, at least some of said attenuating elements having an end coupled to a movable core of a coil energized by a control device.

10. The apparatus according to claim 8 wherein some of said attenuating elements comprise a resilient tongue having an end attached to a leg of a U-shaped coil core and having a remaining end including a plate of magnetic material extending above a remaining leg of said U-shaped coil core.

11. The apparatus according to claim 10 wherein each resilient tongue is elastically connected to adjoining attenuating elements not coacting with said U-shaped coil core.

12. The apparatus according to claim 8 wherein some of said attenuating elements comprise a piëzoelectric element having an end mounted to said slit diaphragm and responsive to a voltage applied thereto by said control means for arching a free end into said slit diaphragm.

13. The apparatus according to claim 8 wherein a free end of each attenuating element is coated with an X-ray attenuating material.

14. The apparatus according to claim 2 wherein said X-ray detector means is a stationary X-ray screen scanned by a photosensitive detector comprised of a plurality of juxtaposed sections moved in synchronism with scanning motion of said X-ray source and said slit diaphragm.

15. The apparatus according to claim 2 wherein said X-ray detector means is a stationary X-ray screen coupled in light-tight fashion to a film cassette and wherein a second X-ray detector means is mounted behind said film assembly to collect X-rays and convert said X-rays into corresponding amounts of light measured by a series of photosensitive elements and converted into corresponding electric signals, said second X-ray detector means being in synchronization with said X-ray source and slit diaphragm means.

16. The apparatus according to claim 2 wherein said X-ray detector means is an elongate image intensifier tube of a proximity focus type moving in synchronism during scanning by said X-ray source and said slit diaphragm and converts sensed X-rays into a light image; and wherein said X-ray detector means comprises a series of photosensitive elements viewing an associated portion of said light image to produce an electrical signal proportional to said light.

* * * * *